US005092168A

United States Patent [19]
Baker

[11] Patent Number: 5,092,168
[45] Date of Patent: Mar. 3, 1992

[54] MONITORING FABRIC PROPERTIES

[75] Inventor: Bernard S. Baker, Coventry, United Kingdom

[73] Assignee: Courtaulds PLC, London, England

[21] Appl. No.: 585,073

[22] PCT Filed: Apr. 13, 1989

[86] PCT No.: PCT/GB89/00376

§ 371 Date: Oct. 11, 1990

§ 102(e) Date: Oct. 11, 1990

[87] PCT Pub. No.: WO89/09935

PCT Pub. Date: Oct. 19, 1989

[30] Foreign Application Priority Data

Apr. 14, 1988 [GB] United Kingdom ............... 8808846

[51] Int. Cl.⁵ .................................. G01N 33/36
[52] U.S. Cl. ....................................... 73/159; 364/470
[58] Field of Search ................. 73/159, 160; 364/470

[56] References Cited

U.S. PATENT DOCUMENTS

| | | | |
|---|---|---|---|
| 3,000,438 | 9/1961 | Alexander | 73/159 |
| 3,857,023 | 12/1974 | McCall | 364/470 |
| 4,058,962 | 11/1977 | Spescha et al. | 73/160 |
| 4,393,701 | 7/1983 | Lawson | 73/160 |
| 4,566,319 | 1/1986 | Yamazaki et al. | 73/160 |
| 4,586,372 | 5/1986 | Massen | 73/159 |
| 4,764,876 | 8/1988 | Whitener, Jr. et al. | 364/470 |
| 4,903,528 | 2/1990 | Balakrishnan et al. | 73/159 |

FOREIGN PATENT DOCUMENTS

| | | | |
|---|---|---|---|
| 0277694 | 8/1988 | European Pat. Off. | 73/159 |
| 3402181 | 7/1985 | Fed. Rep. of Germany | 73/160 |
| 83/02665 | 8/1983 | World Int. Prop. O. | |

OTHER PUBLICATIONS

Ing. et al., "The Properties of the Auto Correlation Function and the Procedure by Which it is Calculated", Melliand Textilberichte, vol. 52, No. 8, pp. 886-891 (Aug. 1971).

Primary Examiner—William A. Cuchlinski, Jr.
Assistant Examiner—Diego F. F. Gutierrez
Attorney, Agent, or Firm—Howson and Howson

[57] ABSTRACT

The present invention relates to a novel method and apparatus for determining the periodicity of a changeable characteristic of a textile fabric. The method includes the steps of sensing a property related to the characteristic at pairs of positions which are spaced apart by a distance, S, along a length of the fabric and generating signals representative of the magnitude of the property at the positions. The generated signal values are stored and the products of the signals generated at each pair of positions are summed in accordance with the formula:

$$\Sigma X_{(y)} \cdot X_{(y+s)}$$

from $y=O$ to $y=Y$ where the parameters are defined in the specification. These steps are repeated for different dimensions, S. The value of S at which the summation of the signals is a maximum is determined and used to generate an output signal representing the value of the periodicity. The method provides information useful for controlling fabric treatment processes such as stentering or compacting, and in particular, for counting the courses of a fabric.

12 Claims, 1 Drawing Sheet

MONITORING FABRIC PROPERTIES

BACKGROUND OF THE INVENTION

1. Field of the Invention

This invention relates to the determination of the periodicity of a characteristic of a textile fabric which changes in a repeating fashion along the length of the fabric. Information relating to such a characteristic can be used to control fabric treatment processes, such as stentering or compacting, for example, to adjust the number of courses of the fabric per unit length to a desired value.

The term "characteristic" is taken to refer to any feature of the fabric (irrespective of whether the fabric is knitted or woven) which repeats itself. For example the feature may be a structural feature such as the courses or warp threads of the fabric, or a repeating pattern such as stitches, holes (in lace for example), dyed regions or different coloured threads, or some other structural feature of the fabric. For simplicity, the invention will be described with reference to counting the courses of a fabric but the present invention is intended to cover other uses, where the context fits.

The present invention is particularly useful for counting the courses of a fabric. The course count of a woven fabric is the number of picks in a unit length of the fabric, and the course count of a knitted fabric is the number of courses in a unit length of the fabric.

2. Description of Prior Art

In some processes for the treatment of fabrics, such as stentering used to stretch or shrink the fabric or compacting (used to shrink the fabric) to obtain uniformity of spacing of the courses and wales (or warp and weft threads) it is necessary to adjust the process parameters to compensate for variations in the fabric entering the process equipment.

In a stenter, the fabric is stretched or overfed as it is passed through a heating zone on pin chains. This is usually achieved by controlling the speed of rotation of rollers over which the fabric passes as it enters and leaves the heating zone and the fabric is held taut on the pin chains to achieve uniform density.

In both of these processes, it is very difficult to count all the courses accurately and to use this count to control the rate of feed of the fabric into, and out of, the stenter or compactor. Not only are the courses irregularly spaced but the fabric may also be puckered, folded, loose or taut.

A previous method of determining course count has employed a photoelectric cell to measure the transparency of the fabric along its length and means for measuring the peak amplitudes of the response curve of the cell thus obtained. Such curves are very irregular in shape and for many purposes, the reliability of the period measurements obtained in this way is not sufficiently high.

In the case of a course count determination, a typical signal will comprise one or more periodic components directly related to the course count, together with other random and/or repetitive components which may completely mask the course count component, at intervals.

The basic course count frequency may be difficult to measure by this known method of counting the signal peaks above a chosen threshold level since:

(a) peaks above the threshold level may be generated by a combination of unrepresentative signals and the basic signal, and
(b) the basic signal may not be present all the time (for example, because the expected apertures in the fabric are obscured).

Furthermore the maximum accuracy of periodicity measurement by this method is determined by the number of courses counted in any one sample length.

It is an object of the present invention to improve the reliability of determinations of the periodicity of a characteristic of a textile fabric such as its course count.

SUMMARY OF THE INVENTION

According to one aspect of the present invention, a method of determining the periodicity of a changeable characteristic of a textile fabric is characterised by the steps of:

(a) sensing a property related to the said characteristic at pairs of positions which are spaced apart by a distance, S, along a length of the fabric,
(b) generating signals representative of the magnitude of the said property at the said positions,
(c) summing the products of the signals generated at each pair of positions in accordance with the formula:

$$\rightarrow x_{(y)} \cdot r_{(y+S)}$$

from $y=0$ to $y=Y$
where $x_{(y)}$ represents the value of the said property at a position y along the fabric, and $r_{(y+S)}$ represents either the value of the said property at a position $(y+S)$ along the fabric, or the value of another regularly varying function, at the position $(y+S)$ along the fabric, (d) repeating steps (a) to (c) for different dimensions, S, and
(e) determining the value of S at which the summation of the signals is a maximum and using this value of S to generate an output signal representing the value of the periodicity.

The present invention is based on the use of correlation methods to detect periodicity in a composite signal which may, for example be derived from the structure variations of a fabric in the direction of movement of the fabric. The periodicity may be used to control, for example, a stenter feed mechanism to correct course frequency errors.

One possible procedure in accordance with the invention is based on analysis of all, or part, of an auto-correlation function of the composite signal.

The auto-correlation function is defined as:

$$T_{(y)} = \underset{Y \to \infty}{\text{LIMIT}} \frac{1}{2Y} \int_{y1}^{y2} x_{(y)} \cdot x_{(y+S)} dy$$

In the case of a course count determination in a fabric:
$x_{(y)}$ is a function x representing the composite signal at a position y along the fabric
$x_{(y+S)}$ is a function x representing the composite signal at a position $y+S$ along the fabric
$Y=$ length along the fabric
$S=$ an interval of length along the fabric.

The function $T_{(y)}$ will exhibit peaks at values of S corresponding to the periods and multiples thereof of repetitive events in the original composite signal $x_{(y)}$. In the case of a fabric, one of those periods will be due to the "course frequency" or a multiple of "course frequency".

Another possible procedure is based on a cross-correlation function analysis using the integral:

$$T_{(y)} = \frac{1}{2Y} \int_{Y_1}^{Y_2} x_{(y)} \cdot r_{(y+S)} dy$$

where $r_{(y+S)}$ is a periodic reference function, for example a sine function.

Peaks will occur in the cross-correlation function $T_{(y)}$ when the period of the reference signal is equal to a period occurring in the composite signal $x_{(y)}$. Hence by evaluating $T_{(y)}$ over a range of reference signal periods covering a predetermined expected period in the composite signal $x_{(y)}$, an actual period in $x_{(y)}$ can be found.

Since a sufficiently accurate assessment of periodicity in relatively small samples can be very reliably made using correlation methods, the method can be used to control machinery such as a stenter, to reduce course frequency variations in the processed fabric to a more acceptable level. This can be achieved by, for example, measuring the course period of the cloth being fed to the stenter and controlling the rate of feed to the stenter pin-chain to correct deviations from nominal course period.

BRIEF DESCRIPTION OF THE DRAWING

The invention will be further described, by way of example, with reference to the accompanying drawing, which shows diagrammatically a stenter control system according to the invention.

DESCRIPTION OF THE PREFERRED EMBODIMENT

Figure 1:
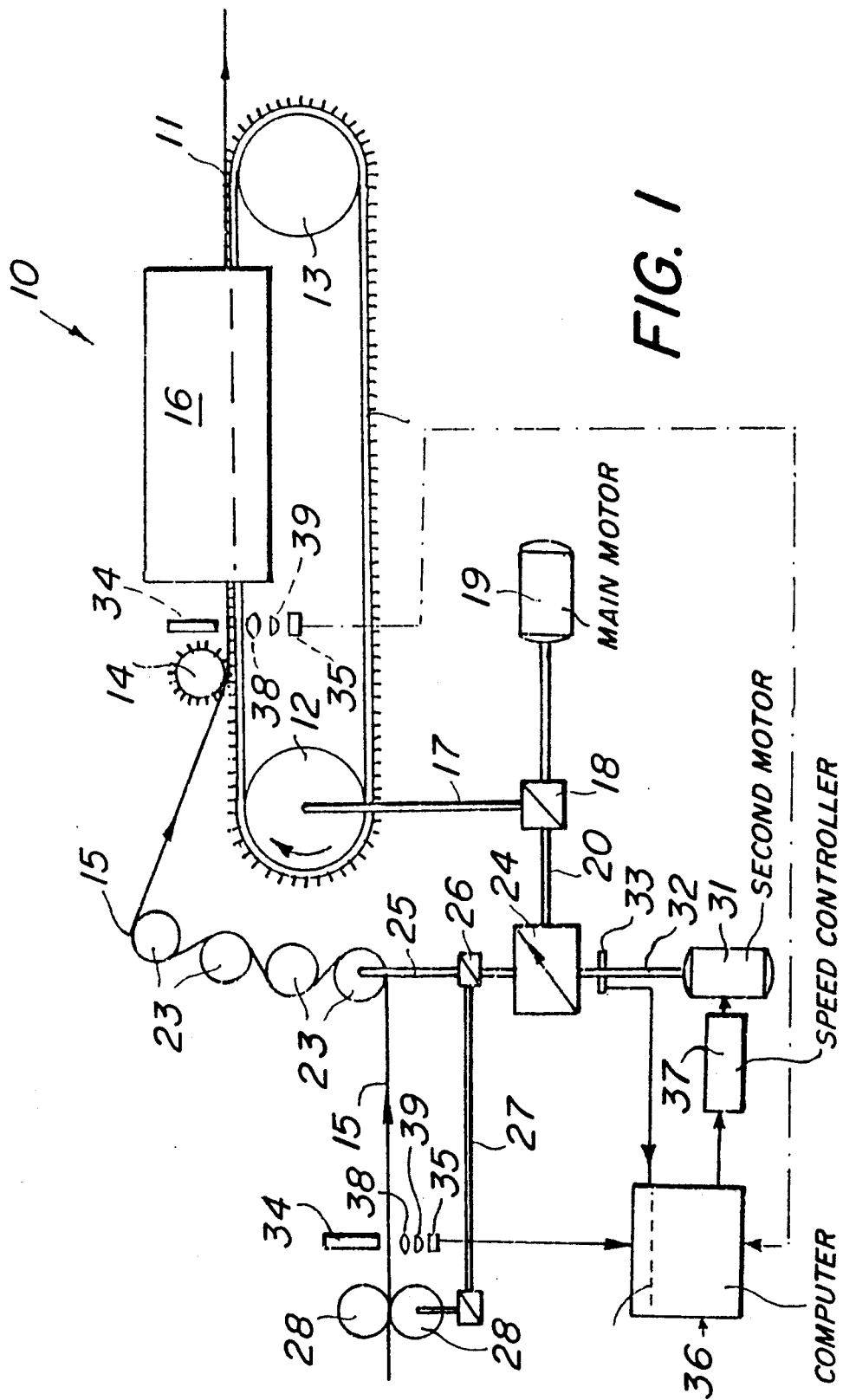

The apparatus illustrated comprises a stenter 10 having a pin-chain 11 carried on rollers 12 and 13, a rotary brush 14 to press fabric 15 onto the pin-chain 11, and a heating chamber 16. The roller 12 (and thus the pin-chain 11) is driven by a shaft 17 from a gear box 18 which is driven by a main drive motor 19. A further output shaft 20 of the gear box 18 drives a set of coupled feed rollers 23 which feed the fabric 15, the shaft 20 being connected through a variable speed gear box 24 to a shaft 25 which is connected to one of the rollers 23 through further gearing 26. A drive shaft 27 also connected to the gearing 26 drives a pair of feed rollers 28, in nip relationship, at the same circumferential speed as the roller 23. The rotary brush 14 is drivably coupled to the feed rollers 23 so that it is driven at the same speed as those rollers.

The variable speed gear box 24 is controlled by an electric motor 31 on whose shaft 32 is mounted a position sensor 33. A light source 34 is arranged to direct a beam of light at the fabric between the feed rollers 28 and the feed rollers 23. A photo-detector 35 is located on the opposite side of the fabric to receive light from the source 34. The output of the photo-detector 35 is supplied to a computer 36. The output of the shaft position sensor 33 is also supplied to the computer 36 and the output of the computer 36 is fed to a motor controller 37 which controls the motor 31.

The computer 36 stores and analyses the composite signal from the photo-detector 35 and computes the course count period. This is compared with the required periods entered via a computer keyboard (not shown) and any difference causes the computer to change the gear ratio of the gear box 24, through the controller 37 and motor 31, so as to correct the error by adjusting the rate of feed of fabric 15 to the pin-chain 11 of the stenter 10.

Referring to the drawing, the photo-detector 35 may be arranged to measure either the transparency or reflectivity of the fabric 15; the choice being dependent on the opacity of the fabric. The area and shape covered by the photo-detector 35 is chosen to effect the degree of signal averaging deemed appropriate for the resolution required. A lens system comprising a part-spherical lens 38 and part-cylindrical lens 39 focuses the light onto the photo-detector 35. The use of the part-cylindrical lens defocuses the wales and accentuates the courses.

The continuous signal from the photo-detector 35 is sampled and digitised at intervals of fabric length in the direction of fabric movement. The intervals must be sufficiently small to resolve the variations in the photo-detector signal. The digitised values are stored in order of occurrence in the computer memory (e.g. in an array schematically indicated at 42). When the sample is fully digitised, the values are read off in pairs, the members of each pair being separated by a fixed number of values in the array corresponding to a length S of fabric. Starting with a pair at array values O and (O+S), the members of each pair are multiplied together for values between y and (y+S). That is, if the storage array containing the digitised signal values is called A, and has K elements, then $A_{(n)}$ is multiplied by $A_{(n+S)}$ for all values of n from n=1 to n=(K−S), and the products summed for each of a range of values of S. This is repeated for a range of values of S, which includes the expected value of the periodicity of the course count. If the values of the product sums were to be plotted against S, any periodicities in the original signal would show as peaks in the curve, the value of S at these points indicating the period. Since the approximate value of the required period in the original sample is known, a precise value of the actual period of the course count can be obtained by detecting the peak value of the product sum in the region of S corresponding to the required period.

The measurement of periodicity of the course count is thus obtained by comparing the values of the product sums in the computer and choosing the maximum value in the range close to the expected value of S which has been sampled. This value of the periodicity is then compared in the computer with the value of the course count required in the finished fabric and the difference signal produced is used, as mentioned above, to control the variable speed gear box 24 through the controller 37 and motor 31. The shaft position sensor 33 feeds back to the computer 36 the actual adjustment of the gear box 24 so that the computer can recognise when the correct ratio adjustment has been achieved in the gear box. The speed with which the fabric 15 is fed to the stenter 10 is thus adjusted and therefore the degree of stretch applied to the fabric 15 in feeding it to the stenter 10. The course count of the fabric 15 can thus be adjusted to the required value.

Where the photo-detector 35 is located in advance of the rollers 23 (indicated with continuous lead lines) a delay in making the adjustment can be achieved in the computer 36 to allow for the fact that the measurement of the actual periodicity in the fabric is determined by the photo-detector 35 in advance of the position between the feed rollers 23 and the pin-chain 11 at which the degree of stretch in the fabric 15 is controlled, so that the appropriate adjustment is applied to the correct length of fabric.

The summation of the products $A_{(n)} \cdot A_{(n+S)}$ effected in the computer 36 is equivalent to performing the summation:

$$\Sigma x_{(y)} \cdot x_{(y+S)}$$

from $y=0$ to $y=Y$, and the following procedures in the computer described above amount to determining for what value of S the summation is a maximum.

If the cross-correlation procedure is to be used, a desired periodic function, for example a sine wave, is stored in the computer memory and the product computed is then $A_{(n)} \cdot r_{(y+S)}$ where r is the periodic function chosen for the cross-correlation. This product is summed from $n=0$ and $y=0$ to $y=Y$ where the values of y are chosen to correspond to the values of n, and Y corresponds to $n=K-S$ using the notation set out above.

The photo-detector 35, that is the point at which the signal representative of the characteristic to be used for control is obtained, may be located either upstream (shown with solid lead lines) or downstream (shown with dashed lead lines) of the correction mechanism (in this case the feed rollers 23 to the stenter). The advantage of generating the signal downstream of the correction mechanism is that the error in the characteristic to be controlled, in this case the course period, will be small and the range in the values of S for which summations must be carried out will thus be reduced. A consequence of this is that the number of computations required to find the relevant peak will be reduced. Monitoring the relevant characteristics after the control region (where the correction mechanism is located) entails that no delay should be introduced between the completion of the computation and the effecting of the control operation.

In order to compute the accuracy of a course count in a fabric with an accuracy of ±0.5% it is necessary to sample an opacity signal at a rate of 200 samples per course and this may require sampling and digitising rates which are difficult to achieve. Adequate signal information can be derived using far fewer samples from the signal curve and generating intermediate values between the samples by interpolation between the sample values. This technique requires fewer analogue-to-digital conversion operations than digitising the same number of sample values of the curve.

Thus, when producing values related to the magnitude of a property in order to carry out the summation mentioned above, some of those values may be derived directly from a signal curve representing the property sensed and others may be derived, by means of intermediate computations, from values of the property sensed which themselves are derived directly from the signal curve. Interpolation between pairs of directly derived signal values is a convenient form of intermediate computation.

I claim:

1. A method of determining the periodicity of a changeable characteristic of a textile fabric characteristic by the steps of:
    (a) sensing a property related to the said characteristic at pairs of positions which are spaced apart by a distance, S, along a length of the fabric.
    (b) generating signals representative of the magnitude of the said property at the said positions,
    (c) storing the generated signal values,
    summing the products of the signals generated at each pair of positions in accordance with the formula:

$$\Sigma x_{(y)} \cdot x_{(y+S)}$$

from $y=0$ to $y=Y$ where $x_{(y)}$ represents the value of the said property at a position y along the fabric and $X_{(y+S)}$ represents either the value of the said property at a position $(y+S)$ along the fabric, or the value of another regularly varying function at the position $(y+S)$ along fabric,
    (e) repeating steps (a) to (d) for different dimensions, S, and,
    (f) determining the value of S at which the summation of the signals is a maximum, and using this value of S to generate an output signal representing the value of the periodicity.

2. A method according to claim 1 wherein step (c) comprises the step of deriving the product of each pair of signals.

3. A method according to claim 1, wherein the value of the periodicity that corresponds to the value of S at which the sum of the pairs of signals is a maximum, is compared with a predetermined periodicity, and the difference is used to generate a difference signal which is used to affect process conditions to which the fabric is subjected, and thereby tend to reduce the said difference.

4. A method according to claim 1, wherein the characteristic is the count of the number of courses of the fabric.

5. A method according to claim 4, wherein the property monitored is the optical transparency of the fabric, and the signals generated at each of the positions is representative of the courses which pass an optical transparency monitor.

6. A method according to claim 1, wherein the analysis of the signals generated in step (b) is based on an auto-correlation function defined by the integral $$T_{(y)} = \underset{Y \to \infty}{\text{LIMIT}} \frac{1}{2Y} \int_{Y1}^{Y2} x_{(y)} \cdot x_{(y+S)} dy$$

where:
    $x_{(y)}$ is a function x representing a composite signal at a position y along the fabric,
    $x_{(y+S)}$ is a function x representing the composite signal at a position $y+S$,
    Y = length along the fabric, and
    S = an interval of length along the fabric.

7. A method according to claim 1, wherein the analysis of the signals generated in step (b) is based on a cross-correlation function defined by the integral:

$$T_{(y)} = \frac{1}{2Y} \int_{Y1}^{Y2} x_{(y)} \cdot r_{(y+S)} dy$$

where:
    $x_{(y)}$ is a function, representing a composite signal at a position y along the fabric,
    Y = length along the fabric,
    S = an interval of length along the fabric and, $r_{(y+S)}$ is a periodic reference function.

8. A method according to claim 6, wherein the output signal is used to control machinery to reduce variations in the course frequency of a processed fabric.

9. Apparatus for carrying out a method of determining the periodicity of a changeable characteristic of a textile fabric, said apparatus comprising, sensing means for sensing a property related to said characteristic at pairs of positions which are spaced apart by a distance, S, along a length of the fabric, a generator for generating signals representative of the magnitude of the said property at the said positions, storing means for storing the generated signal values, summation means for summing the signals generated at each pair of positions in accordance with the formula:

$$\Sigma x_{(y)} \cdot X_{(y+S)}$$

from $y=0$ to $y=Y$ where $x_{(y)}$ represents the value of the said property at a position y along the fabric and $X_{(y+S)}$ represents either the value x of the said property at a position $(y+S)$ along the fabric or the value of another regularly varying function at the position $(y+S)$ along the fabric, and output means for determining the value of S at which the summation of the signals is a maximum and using this value of S to generate an output signal representing the value of the periodicity.

10. Apparatus according to claim 9, wherein the summation means includes means for deriving the product of each pair of signals.

11. Apparatus according to claim 9, further including a comparator for comparing a first signal indicative of the value of the periodicity that corresponds to the value of S at which the sum of the pairs of signals is a maximum, with a second signal indicative of a predetermined periodicity, said comparator being operable to generate an output signal indication of the difference between the first and second signal which is used to affect process conditions to which the fabric is subjected, and thereby tend to reduce the said difference.

12. Apparatus according to claim 9, wherein optical means (34, 35, 38, 39) is provided for monitoring the optical transparency of a fabric characterized by courses, and the signals generated at each of the positions is representative of the courses which pass the optical means (34 35, 38, 39).

* * * * *

UNITED STATES PATENT AND TRADEMARK OFFICE
CERTIFICATE OF CORRECTION

PATENT NO. : 5,092,168
DATED : March 3, 1992
INVENTOR(S) : Bernard S. Baker It is certified that error appears in the above-identified patent and that said Letters Patent is hereby corrected as shown below:

Col. 2, line 28, in the equation, delete "+" and insert -- Σ --.

Col. 6, Claim 1, line 8, in the equation, add -- ( -- before "y+S)".

Signed and Sealed this

Eighth Day of June, 1993

Attest:

MICHAEL K. KIRK

*Attesting Officer*    Acting Commissioner of Patents and Trademarks